United States Patent [19]

Simon

[11] 4,251,631
[45] Feb. 17, 1981

[54] CROSS-LINKED ENZYME MEMBRANE

[75] Inventor: Shulamith Simon, Ramat Gan, Israel

[73] Assignee: Research Products Rehovot Ltd., Rehovot, Israel

[21] Appl. No.: 8,894

[22] Filed: Feb. 1, 1979

[30] Foreign Application Priority Data

Feb. 23, 1978 [IL] Israel .......................... 54116

[51] Int. Cl.³ .................... C12P 13/04; C12N 11/08; C12M 1/40; C12N 9/76
[52] U.S. Cl. ...................... 435/106; 435/95; 435/137; 435/176; 435/180; 435/190; 435/213; 435/288; 435/280
[58] Field of Search ............... 435/174, 176, 177, 180, 435/181, 288, 137, 213, 190, 69, 95, 106, 280

[56] References Cited

U.S. PATENT DOCUMENTS

| | | | |
|---|---|---|---|
| 3,705,084 | 12/1972 | Reynolds | 435/180 |
| 3,796,634 | 3/1974 | Haynes et al. | 435/180 |
| 3,804,719 | 4/1974 | Messing | 435/176 |
| 3,977,941 | 8/1976 | Vieth et al. | 435/180 |
| 4,102,746 | 7/1978 | Goldberg | 435/288 X |

FOREIGN PATENT DOCUMENTS 1183260  3/1970  United Kingdom .

OTHER PUBLICATIONS

Silman et al., Papain Membrane on a Collodion Matrix Science, vol. 150, 1965 (pp. 758–760).
Simon et al., Effectiveness of Enzyme—Membrane Filtration Reactors, Biotechnological Applications of Protein and Enzymes, Academic Press, N.Y., 1977 (pp. 169–181).
Zaborsky, O., Immobilized Enzymes, CRC Press, Cleveland, Ohio, 1973 (pp. 61–74).

*Primary Examiner*—David M. Naff
*Attorney, Agent, or Firm*—Millen & White

[57] ABSTRACT

A cross-linked enzyme membrane is prepared by directly adsorbing enzymes into the pores of a microporous non-fibrous filter membrane made of a silica modified vinylchloride polymer and then cross-linking the enzyme with a bi-functional coupling agent whereby enzyme molecules are cross-linked to each other without chemically bonding the enzyme molecules to the membrane. The cross-linked enzyme membrane is used to carry out enzymatic reactions by passing a solution of substrate for the enzyme through the membrane under a pressure differential.

15 Claims, No Drawings

CROSS-LINKED ENZYME MEMBRANE

BACKGROUND OF THE INVENTION

The present invention relates to a method for the performance of enzymatic reactions and to novel immobilized-enzyme flow-through reactors especially adapted therefor.

In Israel specification No. 46 178 filed 3.12.1974 there is described and claimed a method for the performance of enzymatic reactions. The present invention constitutes a modification of and improvement on the invention described in said earlier specification, the present invention being based on the discovery of cross-linked enzyme membranes utilizable in said method and having unexpectedly superior properties.

As is known the advantage of utilising insoluble enzymes for enzymatic reactions resides in the possibility of acting catalytically with an enzyme on a substrate stream in a continuous way without the need for separating the enzyme from the product obtained by the catalytic reaction.

The use of insoluble enzymes for the performance of enzymatic reactions is known. Thus, for example the following known methods of use should be mentioned:

1. The insoluble enzyme particles are suspended in a tank with stirring, the out-going flux passing through a filter.
2. The insoluble enzyme particles are packed into a column through which the substrate continuously flows.

Both systems were studied by various groups and in many cases, diffusion limitations, resulting from unstirred layers inside and around the particles were observed. These limitations become more important when the diffusion rate of the substrate is slowest and enzymatic reaction rates are highest. Thus it has been found that these diffusional limitations lower the efficiency of the insolubilized enzyme particles, and sometimes only a small percent of their potential activity is used. Consequently it has been desirable to find a method for the performance of enzymatic reactions by means of insoluble enzymes, substantially avoiding the disadvantages of the known processes.

SUMMARY OF THE INVENTION

According to the present invention there has now been found a method for the performance of enzymatic reactions which comprises applying pressure to an aqueous solution of a substrate, which substrate may be chemically altered by way of an enzymatic reaction, causing thereby said solution to flow under a pressure differential through a cross-linked enzyme membrane wherein said cross-linked enzyme membrane is a microporous non-fibrous filter membrane made of a silica modified vinylchloride polymer which polymer is selected from the group consisting of polyvinyl chloride, vinylchloride-propylene copolymer and vinylchloride-vinyl acetate copolymer in the pores of which membrane an enzyme capable of bringing about said chemical alteration in said substrate has been cross-linked by means of a bi-functional coupling agent.

DETAILED DISCUSSION

An aqueous solution in connection with the present invention means a solution in which the amount of water is sufficient to enable the enzymatic reaction. In some cases the substrate is not sufficiently soluble in water and then another solvent, e.g., ethanol, has to be added. In most cases however, the solvent will comprise at least 50% of water.

The present invention also provides an exceptionally and unexpectedly efficient immobilized-enzyme flow-through reactor adapted for the performance of enzymatic reactions on substrates which may be chemically altered by way of an enzymatic reaction comprising a microporous non-fibrous filter membrane made of a silica modified vinylchloride polymer which polymer is selected from the group consisting of polyvinyl chloride, vinyl chloride-propylene copolymer and vinyl chloride-vinyl acetate copolymer in the pores of which membrane an enzyme capable of bringing about said chemical alteration in said substrate has been cross-linked by means of a bi-functional coupling agent.

Enzyme membranes have been prepared and described in the literature, e.g., in Goldman et al. Science Vol. 150 p. 758-760 (1965) and DOS No. 1,915,970 (Avrameas et al.) however said publications are directed to the preparation and study of biological membranes under diffusion conditions and the microenvironmental surroundings of such membranes, and do not propose or suggest the method or novel enzyme-membranes of the present invention and the superior results achieved therewith.

Another publication of interest is British Pat. No. 1,183,260 directed to insolubilised enzymes and their preparation and use. More specifically, said patent describes a method for carrying out enzymatic reactions using enzymes which are chemically bonded to an insoluble support. Of special interest is the fact that this patent specifically mentions the Goldman et al. article and after considering its teachings assumes that the approach of using cross-linked enzymes trapped in a membrane for carrying out enzymatic reactions will not be practical and instead chooses to directly covalently bond enzymes to membranes.

Contrary to the teachings and assumptions of said patent the process of performing enzymatic reactions according to the present invention has now been found to have many advantages when compared with the methods mentioned above, which are based on the use of insoluble enzyme particles or covalently bound enzyme membranes.

Most prior art designs of immobilized-enzyme reactors are based on enzyme particles, in which diffusional resistances play a significant role.

Unlike soluble enzymes, matrix-supported enzymes act in a heterogenous environment, and five distinct steps can be identified in the overall enzymatic process:

(1) diffusion of the substrate from the bulk phase to the carrier-surface (external diffusion).

(2) transport of the substrate from the carrier-surface to the domain of the enzyme-(internal diffusion).

(3) enzyme-catalysed conversion of the substrate, (4) transport of the product from the internal enzyme-filled pores to the particle surface (5) diffusion of product from particle surface to bulk phase.

Steps 1 and 5 are external or bulk diffusional effects which result from the presence of a near-stagnant layer of fluid around the surface of the matrix-supported enzyme. Transport of substrate through this region occurs mainly by molecular diffusion, and results in diffusional resistances. Bulk diffusional limitations have been observed in the case of small packed columns and in the case of enzyme-membranes. High molecular-weight substrates are more strongly effected by diffusional hindrances because of their low diffusivity. Thus, decreased activity was observed for bound papain, ficin and chymotrypsin acting on casein in comparison with their activity on low-molecular weight substrates.

Steps 2 and 4 are internal or pore diffusional effects which result from the fact that the major part of the immobilized enzyme is attached in the interior of the porous carrier matrix and the substrate or product have to diffuse in and out of narrow internal enzyme containing pores to reach or to leave the reaction site. In many cases, these internal diffusional resistances substantially reduce the expressed catalytic activity of the enzyme. Thus, enolase covalently attached to a porous carrier exhibits only a fourth of its potential activity because only that portion of the enzyme is located near the surface of the carrier and displays activity.

Internal diffusional restrictions may also lead to increased product inhibition, because of the slow diffusion of reaction products from the micro-environment. This was observed for the hydrolysis of esters of amino acids by proteolytic enzymes. The hydrogen ions formed by the enzymatic-reaction cause a decrease in the local pH, compared to the bulk pH, which results in a shift in the pH-activity curve. Such displacements in pH-activity profiles were observed for papain, trypsin, chymotrypsin and glucose oxidase.

As stated hereinbefore, it has now been discovered according to the present invention that most, if not all, of these diffusional limitations can be overcome in an enzymatic reactor based on pressure filtration through microporous membranes in the pores of which enzyme molecules are crosslinked to each other to form a stable tri-dimensional network. The substrate flow into the pores is controlled by a pressure gradient. The enzyme-catalysed conversion takes place inside the pores and the products are removed as they are formed. The diffusion-based steps of the processes mentioned above are completely eliminated when microporous membranes with small pore sizes are used. External unstirred layers are absent because the substrate is forced to flow into the pores by a pressure gradient, and internal pore diffusion is negligible because of the small radius of the pores.

The elimination of external and internal mass-transport restrictions in the above described pressure-driven enzymatic-membrane reactors, results in a substantial increase in the biochemical efficiency:

(a) because the reaction process will be kinetically controlled and not diffusionally controlled; and (b) because the enzymes confined within the pores of the membranes are available for catalytic reaction in a much more efficient way than enzymes bound to porous particles, where, because of pore-diffusion limitations, the reaction is often restricted to the particle surface only.

Furthermore, the large pore-wall surface to pore volume ratio ($2.10^5$ for a pore of $0.1\mu$ diameter) results in a very high local concentration of enzyme in the pore. If we assume the pores to be identical straight cylinders and if we assume that the enzyme molecules cover the pore walls in a dense mono-molecular layer, then the enzyme concentration can be calculated as follows:

Enzyme concentration
$(M/cc) = (A/a)/VN = 2/(a \cdot r \cdot N)$

A = Pore-wall surface
a = Surface of enzyme molecule = $X^2$ (X = 100 A°)
V = Pore volume
N = Avogadro's number
r = pore radius.

Enzyme concentration in an $0.1\mu$ pore-size membrane would be 0.6 M/cc. Translated into mg's, this would mean 15 mg$\mu$ of an enzyme with a molecular weight of 25,000 (i.e. chymotrypsin). This high local concentration results in a high conversion rate of substrates.

The use of the cross-linked enzyme-membrane according to the present invention also has, inter alia, the following advantages when being compared with the covalently bound enzyme membrane described and claimed in British Patent Specification No. 1,183,260:

1. The loading capacity of the membrane i.e., the amount of cross-linked enzyme insolubilized per unit of membrane, is larger. The enzyme molecules form a close-packed layer on the pore surface, thus achieving a very high local concentration of enzyme in the pore;

2. The tri-dimensional network of the enzyme in the membrane strengthens the matrix and increases the membrane's resistance to compaction as encountered in the method according to the present invention;

3. The cross-linked enzyme is more stable to heat denaturation and long storage periods than covalently bonded enzymes. Moreover, by crosslinking enzyme molecules with an inactive protein one can add the protective effect of environmental inactive proteins to the stabilizing effect of crosslinking onto a matrix;

4. The crosslinking of enzymes inside a preformed membrane is a general and non-specific method suitable for any matrix and any enzyme. It avoids the need for the formation of active sites on the membrane and requires only an appropriate bifunctional reactive agent.

More recently the immobilization of enzymes by cross-linking on a membrane for use in an enzyme reactor has been described. Thus, e.g., in Inman et al. Biochem. J. (1972) 129, 255–262 there is described the preparation and use of a cross-linked urease nylon membrane through which a substrate is pumped. As stated however in said article the activities obtained were very low and Inman concluded that other support types such as nylon-tube-supported enzyme preparations were preferable over the use of a nylon membrane containing a cross linked enzyme.

Furthermore as shown in Comparative Example 1 hereinafter the activity of the immobilized enzyme membrane according to the present invention is 17 times greater than that of the cross-linked Duralon-nylon membranes used by Inman.

Similarly, while in an article by Bernath and Vieth reported by Olson et al, Immobilized Enzymes in Food and Microbial Processes (1974) Plenum Press N.Y. P. 180–185 there is described the preparation of collagen-based enzyme membranes wherein the immobilization of enzymes on the collagen is accomplished through complexation i.e. non-covalent bonding between the collagen membrane matrix and the enzyme, said collagen membranes cannot be considered as teaching or suggesting the membranes of the present invention or the superior results obtainable therewith.

In fact these membranes are known to be non-porous and the pumping of a substrate through said membranes, if done at all, is by diffusion as can be understood from the description on page 176 ibid wherein the reacted module preferred for use with this type of membrane is described as a spirally wound module in which the flow of substrate is guided across the membrane surfaces through the spiral flow channels formed (cf. Methods in Enzymology Vol. XLIV pp. 251-253). As stated in said article the substrate stream can be pumped in axially through the capillaric channels that are formed by the spiral configuration or through the membrane under forced permeation conditions. However, as is known, forced permeation conditions are not flow-through conditions and are synonymous with diffusion conditions. Thus the membrane and reactor of Vieth work on an entirely different principle and under different conditions than the flow-through membranes and reactors of the present invention wherein the substrate stream is totally filtered through the membrane and the whole enzymatic conversion is conducted in the membrane's pores and not along the membrane's surface.

As stated the present invention is directed to a microporous non-fibrous filter membrane made of a silica modified vinylchloride polymer in the pores of which membrane an enzyme has been cross-linked and the use of such a cross-linked enzyme membrane for the performance of enzymatic reactions.

It has now been unexpectedly found that said membranes, having a pore size in the range of about 0.1 to 2 micron and preferably about 0.1 to 0.5 micron, when used as enzyme carriers for the performance of enzymatic reactions, exhibit properties superior to those observed with other standard filtration membranes. The enzymatic specific activity obtainable per unit area under equal reaction conditions is larger by a factor of 5-10 than that obtained with any other membrane. The exact grade of porosity used depends on the contemplated end-use and substrate viscosity, and is chosen so as to minimize the pressure drop across the reactor at practical flow rates.

Many types of reactors have been employed with immobilized enzymes. These are classified according to mode of operation and the flow pattern in the reactor. As discussed hereinbefore the most common type is the stirred tank, which is usually operated as a batch system but also in a semi-continuous way. Continuous flow-systems are packed beds of enzyme particles or fibers, semi-permeable hollow fibers, or tubular reactors.

In the design of a reactor, the amount of catalytic activity per unit volume of reactor is an important factor, since this determines the size of the reactor. The reaction rate per unit volume is a function of the amount of immobilized enzyme per unit volume, its specific activity and the efficient utilization of that activity.

The reaction rate of the immobilized enzymes is very often limited by the rate of diffusion of substrate from the bulk of the solution to the surface of the immobilized enzymes. Limitations of these kinds have been observed in stirred tanks and in packed beds, where this effect was significant at flow rates lower than 1-2 cm/min.

The reactor according to the present invention is a continuous flow system with an exceptionally high catalytic activity per unit volume. The utilization efficiency of that activity is also exceptionally high. This is so because the mixing of enzyme and substrate is very efficient since the enzymes are immobilized in the pores and the substrate is pressed into the pores, and the rate of diffusion from pore axis to pore wall is always larger than the reaction rate at the pore wall.

Membranes suitable for use in the present invention are already available commercially and marketed by Amerace ® as filtration devices. These membranes are described in the Amerace ® literature as microporous material made of vinylchloride polymers selected from the group consisting of polyvinylchloride, vinylchloride-propylene copolymer and vinylchloride vinylacetate copolymer in which finely divided silicon dioxide is embedded and are more fully described and defined in U.S. Pat. No. 3,862,030.

Thus, while Amerace ® filter material is known and marketed as microporous membranes in various forms as a submicron filter media, it has now been unexpectedly found that said membranes, when loaded with cross-linked enzymes and used as enzyme-carriers for the performance of enzymatic reactions, exhibit properties far superior to the properties observed with the use of standard filtration membranes used to date.

In recently issued U.S. Pat. No. 4,102,746 there is described and claimed a method and means for immobilizing enzymes by coupling or bonding them to an insoluble support or carrier, wherein said support or carrier is in the form of a microporous member that is non-biodegradable and resistant to chemical attack and which microporous material is defined as preferably being the same type of microporous membrane as preferably used in the method and reactor of the present invention, i.e., the type described and defined in U.S. Pat. No. 3,862,030.

The inventor of said patent, however, after particularly noting the different prior art methods of immobilizing enzymes, including the possibility of immobilizing by mechanical entrapment within a semi-permeable carrier, such as, a membrane, specifically chose and limited his invention to enzyme membranes wherein the enzyme is directly or indirectly coupled or bonded to the membrane and more particularly to the filler particles dispersed throughout the membrane matrix.

Contrary to the assumptions and teachings of said Patent, it has now been further found that when enzyme molecules are directly adsorbed on the matrix and then crosslinked to each other by means of crosslinking agents, instead of being chemically bound directly or through a bridging agent to the insoluble microporous support material, there is formed a stable tri-dimensional network of enzyme molecules which can no longer be desorbed during use and which results in the creation of an enzyme reactor having unexpectedly superior properties even over the reactors produced in accordance with the teachings of U.S. Pat. No. 4,102,746, as demonstrated in comparative examples 13-15 hereinafter.

Cross-linked enzyme membranes according to the present invention are prepared by first impregnating the membrane pores with a suitable enzyme. This can be done either by forcing an enzyme solution through the pores of said membrane or by immersing the membrane in the enzyme solution for 3-10 hours; thereby allowing the enzyme molecules to diffuse into the pores of the membrane. The enzyme-loaded membrane is then immersed into a solution of a bi-functional cross-linking agent to effect the cross-linking of said enzyme in said membrane pores.

The enzyme solution preferably has a concentration of 5-50 mg/cc and a pH of 5-9. The enzyme solution may also comprise an inactive protein, e.g., albumin. Said protein protects labile enzymes from inactivation. Moreover, said solution preferably also contains a reversible inhibitor or a substrate which does not contain groups which can react with the cross-linking agent.

The immersion of the membrane into the solution of the cross-linking agent requires about 1-10 hours at about 1°-30° C.

Immobilization of the enzyme is carried out in an aqueous medium at pH conditions and temperatures which do not tend to inactivate the enzyme.

The temperature of choice depends, however, mainly on the particular enzyme used. Usually the temperature can range from 0° to ~30°. A temperature in the range of 10° to 25° C. is preferred. Enzyme concentrations in the solution used to load the membrane are between 0.1-10% by weight, and preferably 0.5-3% by weight.

The amount of crosslinking agent used is dependent on the amount of enzyme to be crosslinked. Usually a 2.5% glutardialdehyde solution is used at pH 6.7.

The membrane is then advantageously washed in a pressure filtration cell in order to remove unbonded enzyme and cross-linking agent. Free aldehyde or other active groups may be blocked by glycine or another suitable blocking agent.

As suitable cross-linking agents there may be mentioned, for example, dialdehydes, e.g. glutaraldehyde; dioxobenzidine; hexamethylenediisocyanates; 1,5-difluoro-2,4-dinitrobenzene; N,N'-hexamethylenebisiodoacetamide, etc.

The enzyme can be of animal or plant origin. Thus there should be mentioned for example hydrolases, e.g., chymotrypsin, trypsin, amylases, carboxy-peptidase, amino acylase and carboxypeptidase; oxidases, e.g., glucose-oxidase, catalase, alcohol dehydrogenase and peroxidase; amidases, e.g., urease, asparaginase; alkaline phosphatase etc.

When an inhibitor is used, said inhibitor is specific for each enzyme. Thus, for example, glucose is used to protect glucose-oxidase; β-phenyl-propionate to protect chymotrypsin; etc.

As stated above the method for performing enzymatic reactions according to the present invention comprises causing an aqueous solution of a substrate which may be chemically altered by enzymatic reaction to flow under a pressure differential through a cross-linked enzyme membrane and any enzyme suitable for causing enzymatic reactions may be utilised as part of the enzyme membrane. Thus, an unrestricted number of possibilities for the performance of enzymatic reactions may be considered. For example the method according to the present invention may be utilised for the resolution of racemic mixtures of amino acid compounds having an acylated amino group and/or an esterified carboxylic group. There, such mixture is forced through the appropriate enzyme-membrane where one isomer is hydrolysed thus yielding a mixture of an L-, or D- optically pure amino acid and of the D- or L- acyl amino acid of the non-hydrolysed isomer, which may be separated by methods known per se.

It is also possible to oxidise glucose to gluconic acid using glucose-oxidase as enzyme.

Moreover, urease may be utilised in order to decompose urea.

Another possibility is to utilise catalase for the decomposition of peroxides.

The pressure required for carrying out the enzymatic reaction depends on the enzyme membrane, the substrate concentration, the desired degree of conversion and/or the desired reaction rate. There is, however, no difficulty in determining the optimum pressure differential for each enzymatic reaction as dictated by the reactants used and the results sought to be achieved. Thus, e.g., with a specific cross-linked enzyme membrane increased pressure will bring about increased reaction rates with decreasing degrees of conversion and optimum results can be regulated in accordance therewith. In practice, it was in fact found that said pressure differentials can range from about 0.05 to about 10 atmospheres and will preferably be in the range of about 0.05 to about 5 atmospheres. As will be recognized said pressure differentials can be obtained either by applying direct pressure to the substrate solution or by maintaining a vacuum pressure on the other side of the cross-linked enzyme membrane.

In a preferred embodiment of the present invention there is prepared an immobilized-enzyme flow-through reactor wherein the membrane is packed into a cartridge to provide a more compact and highly effective reactor.

In an especially preferred embodiment of the present invention the membrane is pleated and packed in a cartridge having a packing ratio of membrane area to cartridge volume of at least 5 cm$^2$/cm$^3$.

The commercially available Amerace ® membrane filter cartridges which use membranes of the type described and which are very compact, having a packing ratio of 5.4 cm$^2$/cm$^3$, are ideally suited for the novel method and reactor of the present invention once enzyme molecules are immobilized on the micropore walls of the membrane in the cartridge by the methods already described hereinbefore.

Thus, the novel use of these membrane-cartridges as supporters for enzymes, which are immobilized on the porewalls of the membrane, provides highly efficient enzyme-reactors and forms a part of the present invention.

As with the membranes themselves substrate is pressed or filtered through the cartridge at low or high flow rates according to desire. The enzymatic reaction occurs in the pores, where a nearly "complete mixing" of substrate and immobilized enzyme exists and such an enzyme-membrane cartridge, when attached to a proper pumping equipment which pumps substrate through the filter reactor, comprises an especially preferred continuous flow-through enzyme reactor since the microporous membrane cartridge design provides a compact, cheap and highly effective reactor, through which substrate can be passed at low or high flow rates, according to desire.

Enzyme reactors of this type are particularly effective for applications comprising transformations of soluble substrates by relatively rapid enzymes; in particular, the production of L-amino acids from DL amino acid derivatives by stereospecifically hydrolyzing one of the derivatives.

While the invention will now be described in connection with certain preferred embodiments in the following examples it will be understood that it is not intended to limit the invention to these particular embodiments. On the contrary it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

EXAMPLE 1—COMPARATIVE MEMBRANE ACTIVITY

The Millipore Duralon ®-nylon membrane (1μ pore size) used by Inman as well as Millipore MF-Cellulose-ester membrane (0.22μ pore size) and Gellman-Acropore ® membrane (a copolymer of acritonitrile and polyvinyl chloride coated onto a nylon web, 0.2μ pore size) were tested as to their specific activities towards various enzymes as compared with an Amerace membrane made of silica modified vinyl chloride polymer (0.3μ pore size). All enzymes were loaded according to the method of loading the membranes of the present invention.

Millipore MF-Cellulose ester and Duralon-nylon, Gellman Acropore and Amerace membranes were immersed in a chymotrypsin solution (30 mg/ml) in phosphate buffer (0.05 M, pH 7.0) for 3 hours. They were then removed from the enzyme solution and immersed in a glutardialdehyde solution of 2.5% for 3 hours. They were then mounted in a pressure cell and washed with water and buffer, to remove non-bound enzyme. Esterase activity was determined at 37°, using a solution of DL-Tryptophane methyl ester solution (10 mM) in phosphate buffer (0.1 M, pH 7.8). This solution was pressed through the membranes at such a rate as to obtain in each case a conversion of 87%. The effluent was collected, and its optical activity measured. Product concentration and membrane activity were calculated. The activity of the Millipore MF-cellulose ester membrane was 0.88 μMoles/min.cm$^2$. The activity of the Millipore Duralon-nylon membrane was 1.0 μMoles/min.cm$^2$. The activity of the Acropore membrane was 0.36 μMoles/min.cm$^2$. The activity of the Amerace Silica modified PVC membrane was 17 μMoles/min.cm$^2$.

EXAMPLE 2

α-amylase was immobilized on various types of membranes. These were made of cellulose esters (Millipore MF type), nylon (Millipore-Duralon type), copolymer of acrylonitrile and polyvinyl chloride (Gellman-Acropore type) and silica modified vinyl chloride polymer (Amerace MPS type). The enzyme solution was pressed through the membrane, cross-linked with glutardialdehyde, washed, and tested for activities. A 0.2% solution of soluble starch was pressed through the membranes at 26° C. and maltose concentration in the effluent determined. The activities of the membranes in mg of maltose produced per unit area at a conversion of 73% were the following:

Cellulose ester membranes (Millipore)—0.36 mg/min.cm$^2$
Nylon membranes (Millipore)—0.43 mg/min.cm$^2$
Acrylonitrile-PVC membranes (Gellman)—0.12 mg/min.cm$^2$
PVC-silica membranes (Amerace)—2.68 mg/min.cm$^2$

EXAMPLE 3

α-amylase membranes were prepared as described in Example 2. A 2% solution of soluble starch was pressed through the membranes and tested at 26° C. The activities in mg of maltose produced per unit area at a conversion of 66% were the following:
Cellulose ester membrane (Millipore)—1.25 mg/min.cm$^2$
Nylon membrane (Millipore)—1.36 mg/min.cm$^2$
Acrylonitrile-PVC membrane (Gellman)—0.45 mg/min.cm$^2$
PVC-silica membrane (Amerace)—6.1 mg/min.cm$^2$

EXAMPLE 4

α-amylase membranes were prepared as described in Example 2. A 2% solution of soluble starch was pressed through the membranes and tested at 37° C. The activities in mg maltose produced per unit area at a conversion of 66% were the following:
Cellulose ester membrane (Millipore)—2.1 mg/min.cm$^2$
Nylon membrane (Millipore)—2.4 mg/min.cm$^2$
Acrylonitrile-PVC membrane (Gellman)—0.87 mg/min.cm$^2$
PVC-silica membrane (Amerace)—20.2 mg/min.cm$^2$

EXAMPLE 5

Thermoamylase (Novo Industries) was immobilized on various types of membranes as described in Example 2. A 2% solution of soluble starch was pressed through the membranes at 65° C. and the activities of the membranes in mgs of maltose produces per unit area at a conversion of 70% were the following:
Cellulose ester membranes (Millipore)—0.5 mg/min.cm$^2$
Nylon membranes (Millipore)—0.65 mg/min.cm$^2$
Acrylonitrile-PVC membranes (Gellman)—0.22 mg/min.cm$^2$
PVC-silica membranes (Amerace)—10.5 mg/min.cm$^2$

EXAMPLE 6

Standard filtration cartridges based on membranes made of cellulose esters (Millipre) acrylnitrile-PVC (Gellman), silica modified PVC (Amerace) were loaded with thermoamylase. A 2% solution of starch was filtered through these thermoamylase reactors and the conversion of starch to maltose measured. The results are given in grams of maltose produced per day:
Cellulose cartridge (1217 cm$^2$)—0.88 kg/cartridge day.
Acrylonitrile-PVC cartridge (4600 cm$^2$)—1.46 kg/cartridge day
Silica modified PVC cartridge (5110 cm$^2$)—77.2 kg/cartridge day

EXAMPLE 7

Bacterial amino-acid ester hydrolase (AAEH) was immobilized on various types of membranes. The membrane's hydrolytic activities were measured using a DL-pheGly methyl ester solution (40 mM) in phosphate buffer (0.1 M, pH 6.0). The specific activities of the various membranes in terms of D-pheGly produced per cm$^2$ at 50% conversion were:
Cellulose ester membranes—3.45 μMoles/min.cm$^2$
Acrylonitrile-PVC membranes—0.61 μMoles/min.cm$^2$
PVC-Silica membranes—21.4 μMoles/min.cm$^2$

EXAMPLE 8

Subtilisin was immobilized as described in Example 2. The membranes were assayed using a solution of N-acetyl DL-Methionine methyl ester (100 mM). The specific activities in N-Acetyl-L-methionine produced per cm$^2$ of the membranes at 76% conversion were:
Cellulose esters—2.6 μMoles/min.cm$^2$
Acrylonitrile-PVC—1.1 μMoles/min.cm$^2$
PVC-Silica—16 μMoles/min.cm$^2$

EXAMPLE 9

Trypsin was immobilized on various membranes as described in Example 2. The specific activities were determined using a solution of benzoyl arginine ethyl ester ($5.10^4\mu$) in phosphate buffer. The obtained activities in Moles of benzoyl Arginine per cm$^2$ at 87% conversion were:
Cellulose ester membranes—1.5 Moles/min.cm$^2$
Acrylonitrile-PVC membranes—0.7 Moles/min.cm$^2$
Silica modified PVC membranes—5.4 Moles/min.cm$^2$

EXAMPLE 10

Silica modified PVC pleated cartridge (membrane area, 5110 Cm$^2$, cartridge volume 955 cm$^3$) was immersed in an AAEH solution 30 mg/ml, for 3 hours, and then in a glutardialdehyde solution (2.5%) for 3 hours. It was washed with water and buffer. A DL PheGly ME solution was filtered through the cartridge at 40° at different flow rates. The amount of D-PheGly in the effluent was measured polarimetrically. The D-PheGly was separated from the L-PheGlyME by methods known per se. The amounts of D-PheGly specifically hydrolyzed per day per cartridge for the different conversion rates of 90%, 85% and 75% were 31, 56 and 83 kg/day respectively.

COMPARATIVE EXAMPLE 11

The cartridges of Amerace (H-30—0.3$\mu$) Millipore (CFGS—0.22$\mu$) and Gellman (0.2$\mu$) with packing densities of 5.35 cm$^2$/cm$^3$, 0.75 cm$^2$/cm$^3$ and 6.4 cm$^2$/cm$^3$ were loaded with chymotrypsin as described in Example 1 and assayed. The activities obtained for a conversion of 85% were: 91 $\mu$moles/cm$^3$.min, 0.7 $\mu$moles/cm$^3$.min, and 4.6 $\mu$moles/cm$^3$min.

COMPARATIVE EXAMPLE 12

The cartridges of Amerace, Millipore and Gellman were loaded with amino acid ester hydrolase as described in Example 7. The activities obtained for a conversion of 50% were: 114 $\mu$moles/cm$^3$.min, 2.5 $\mu$moles/cm$^3$.min, and 7.5 $\mu$moles/cm$^3$.min.

COMPARATIVE EXAMPLE 13

Untreated Amerace microporous membranes (0.5$\mu$) were chemically modified by:
(a) covalent bonding of gamma-aminopropyltriethoxysilane (APTS) according to example 2 of U.S. Pat. No. 4,102,746; and
(b) chemical adsorption of 50,000 mol. wt. branched chain polyethyleneimine (PEI) and chemical treatment with gluterdialdehyde (GA) in accordance with examples 3 and 4 of U.S. Pat. No. 4,102,746. After washing the membranes with water, they were incubated in a solution of 30 mg/ml of chymotrypsin in phosphate buffer (0.05 M) at pH 7.0 for 1 hour.
(c) Another membrane was treated according to the present invention by direct incubation of another untreated Amerace membrane in the same chymotrypsin solution, and subsequent cross-linking in glutardialdehyde, 2.5%, as described in Example 1 hereinbefore.

The membranes were mounted in pressure cells and washed with buffer till no enzyme activity was found in the wash water. They were then assayed for their activity by following the stereospecific hydrolysis of DL-Tryptophane methyl ester obtained when pressing the solution (10 mM) in phosphate buffer, pH 7.8 (0.1 M) through the membranes at 26° C. The flow rate of substrate solution through the membranes was controlled so that an equal conversion was obtained at each case, namely, 81.5%. The activities calculated from the different flow rates were the following:
(a) Membrane activated by APTS: 2.2 $\mu$Moles/min.cm$^2$
(b) Membrane activated by PEI-GA: 2.2 $\mu$Moles/min.cm$^2$
(c) Membrane activated by direct adsorption and cross-linking according to the present invention: 6.7 $\mu$Moles/min.cm$^2$

COMPARATIVE EXAMPLE NO. 14

Activated membranes were prepared according to Example No. 13. The activated membranes as well as the non-treated membrane, were incubated in Alcalase, a commercial liquid enzyme preparation, as described in Example 13. The membranes were assayed by following the asymmetric hydrolysis of N-acetyl-DL-Methionine methyl ester. The solution, 100 mM in phosphate buffer pH 7.8 (0.1 M) was pressed through the various membranes in such rates as to obtain a conversion of 53.8%. The activities of the membranes were:
(a) Membrane activated by APTS: 13.4 $\mu$Moles/min.cm$^2$
(b) Membrane activated by PEI-GA: 15 $\mu$Moles/min.cm$^2$
(c) Membrane activated by direct adsorption and cross-linking according to the present invention: 62 $\mu$Moles/min.cm$^2$

COMPARATIVE EXAMPLE NO. 15

Activated membranes were prepared according to Example No. 13. The activated membranes and an untreated membrane were incubated in a solution of glucose oxidase (30 mg/ml) in buffer phosphate pH 6.0 (0.1 M), as described in Example 13. The membranes were assayed by following the oxidation of glucose to gluconic acid, through titration. A 0.033 M glucose solution in 0.05 M acetate buffer and 0.05 M NaCl was pressed through the membranes at 30.5° C. Oxygen was bubbled through the solution and also used as pressurizing agent. The flow rates of glucose through the membranes were such as to obtain a conversion of 3.8%. 5 ml of NaOH (0.1 M) were added to a sample of the effluent (10 ml) and back titrated with HCl (0.05 M). The activities obtained for the three membranes were:
(a) Membrane activated by APTS: 0.08 $\mu$Moles/min.cm$^2$
(b) Membrane activated by PEI-GA: 0.13 $\mu$Moles/min.cm$^2$
(c) Membrane activated by direct adsorption and cross-linking according to the present invention: 0.73 $\mu$Moles/min.cm$^2$ It will be evident to those skilled in the art that the invention is not limited to the details of the foregoing illustrative embodiments and examples and that the present invention may be embodied in other specific forms without departing from the essential attributes thereof, and it is, therefore, desired that the present examples be considered in all respects as illustrative and not restrictive, reference being made to the appended claims, rather than to the foregoing description, and all changes which come with the meaning and range of equivalency of the claims are, therefore, intended to be embraced therein.

What is claimed is:
1. A method for effecting an enzymatic reaction which comprises causing an aqueous solution of a substrate capable of being chemically altered upon contact with an enzyme to flow under a pressure differential through a cross-linked enzyme membrane, wherein said cross-linked enzyme membrane is a microporous non-fibrous filter membrane having a pore size of between about 0.1 and 2.0 microns and made of a silica modified vinylchloride polymer selected from the group consisting of polyvinyl chloride, vinylchloride-propylene copolymer and vinylchloride-vinyl acetate copolymer, and said cross-linked membrane is formed by directly adsorbing said enzyme into the pores of said microporous nonfibrous filter membrane and then cross-linking the enzyme therein by means of a bi-functional coupling agent, whereby enzyme molecules in the pores are cross-linked to each other but are not chemically bound directly or through a bridging group to the microporous non-fibrous filter membrane.

2. A method according to claim 1, wherein said pressure differential is from about 0.05 to about 5 atmospheres.

3. A method according to claim 1 wherein the enzymatic reaction is a hydrolytic reaction.

4. A method according to claim 3, wherein said hydrolytic reaction comprises the selective hydrolysis of one isomer of a racemic mixture of amino acid compounds having at least one of an acylated amino group and an esterified carboxylic group.

5. A method according to claim 1, wherein the enzymatic reaction is an oxidizing reaction.

6. A method according to claim 1, wherein said enzyme is Chymotrypsin or Trypsin.

7. A method according to claim 1 wherein said membrane is packed in a cartridge.

8. A method according to claim 7 wherein said membrane is pleated and packed in a cartridge having a packing ratio of membrane area to cartridge volume of at least 5 cm$^2$/cm$^3$.

9. A method according to claim 1, wherein the cross-linking agent is selected from the group consisting of dialdehydes, dioxobenzidine, hexamethylene-diisocyanate, 1,5-difluoro-2,4-dinitrobenzene and N,N'-hexamethylene-bisiodoacetamide.

10. A method according to claim 9, wherein the cross-linking agent is glutaraldehyde.

11. An immobilized-enzyme flow-through reactor suitable for effecting an enzymatic reaction comprising a microporous non-fibrous filter membrane having a pore size of between about 0.1 to 2.0 microns and made of a silica modified vinylchloride polymer selected from the group consisting of polyvinyl chloride, vinyl chloride-propylene copolymer and vinyl chloride-vinyl acetate copolymer and having an enzyme immobilized in the pores thereof by directly adsorbing the enzyme in the pores and then cross-linking the enzyme by means of a bi-functional coupling agent, whereby enzyme molecules in the pores are cross-linked to each other but are not chemically bound directly or through a bridging group to the microporous non-fibrous filter membrane.

12. An immobilized-enzyme flow-through reactor according to claim 11 wherein said membrane is packed in a cartridge.

13. An immobilized-enzyme flow-through reactor according to claim 12 wherein said membrane is pleated and packed in a cartridge having a packing ratio of membrane area to cartridge volume of at least 5 cm$^2$/cm$^3$.

14. An immobilized-enzyme flow-through reactor according to claim 11 wherein the cross-linking agent is selected from the group consisting of dialdehydes, dioxobenzidine, hexamethylene-diisocyanate, 1,5-difluoro-2,4-dinitrobenzene and N,N'-hexamethylene-bisiodoacetamide.

15. An immobilized-enzyme flow-through reactor according to claim 14, wherein the cross-linking agent is glutaraldehyde.

* * * * *